United States Patent [19]

Johnson et al.

[11] 3,996,154

[45] Dec. 7, 1976

[54] EMULSIONS OF ISOCYANATES AND THEIR MANUFACTURE

[75] Inventors: Frank Johnson; Alan Metcalfe Wooler, both of Manchester, England; Olle Bengtson, Goteborg, Sweden; Peter Mayrhofer, Manchester, England

[73] Assignee: Imperial Chemical Industries Limited, London, England

[22] Filed: Sept. 27, 1974

[21] Appl. No.: 510,139

[52] U.S. Cl. .............................. 252/312; 156/331; 252/314; 252/356
[51] Int. Cl.² ................... B01J 13/00; B01F 17/42
[58] Field of Search .......................... 252/312, 357

[56] References Cited

UNITED STATES PATENTS

| 2,684,949 | 7/1954 | McMillan et al. ............. 252/312 X |
| 2,948,691 | 8/1960 | Windemuth et al. .......... 252/357 X |
| 3,428,592 | 2/1969 | Youker ......................... 252/312 X |

*Primary Examiner*—Richard D. Lovering
*Attorney, Agent, or Firm*—Cushman, Darby & Cushman

[57] ABSTRACT

Aqueous emulsions comprising organic isocyanates, water and non-ionic surface active agents devoid of hydroxy, amino and carboxylic acid groups and the use of such emulsions for surface coatings. Use of aqueous emulsions of mixed methylene bridged polyphenyl polyisocyanates as bonding agents for the reconstitution of foam scrap.

7 Claims, No Drawings

EMULSIONS OF ISOCYANATES AND THEIR MANUFACTURE

This invention relates to emulsions of organic isocyanates in water and to the preparation and use of such emulsions.

According to the present invention there are provided aqueous emulsions comprising water, organic isocyanate and a non-ionic surface active agent devoid of hydroxy, amino and carboxylic acid groups.

Any organic isocyanate may be used in the emulsions of the present invention; the emulsions of the invention are of particular value when the organic isocyanate is an isocyanate containing a plurality of isocyanate groups.

Examples of monoisocyanates which may be present in the emulsions of the present invention include phenyl isocyanate, tolyl isocyanates, p-butyl phenyl isocyanate, o-and p-methoxy phenyl isocyanate, o-isocyanate benzyl chloride, cyclohexyl isocyanate, octyl isocyanate, chlorohexyl isocyanate.

Examples of organic isocyanates containing a plurality of isocyanate groups which may be present include aliphatic isocyanates such as hexamethylene diisocyanate, aromatic isocyanates such as m- and p-phenylene diisocyanate, tolylene-2,4- and 2,6-diisocyanates, diphenylmethane-4,4'-diisocyanate, chlorophenylene-2,4-diisocyanate, naphthylene-1,5-diisocyante, diphenylene-4,4'-diisocyanate, 4,4'-diisocyanate-3,3'-dimethyldiphenyl, 3-methyldiphenylmethane-4,4'-diisocyanate and diphenyl ether diisocyanate, cycloaliphatic diisocyanates such as cyclohexane-2,4- and 2,3-diisocyanates, 1-methyl cyclohexyl-2,4- and 2,6-diisocyanates and mixtures thereof and bis-(isocyanatocyclohexyl-)methane and triisocyanates such as 2,4,6-triisocyanatotoluene and 2,4,4'-triisocyanatodiphenyl ether.

There may be present mixtures of isocyanates for example a mixture of tolylene diisocyanate isomers such as the commercially available mixtures of 2,4- and 2,6- isomers and also the mixture of di- and higher poly-isocyanates produced by phosgenation of aniline/-formaldehyde condensates. Such mixtures are well-known in the art and include the crude phosgenation products containing mixtures of methylene bridged polyphenyl polyisocyanates, including diisocyanate, triisocyanate and higher polyisocyanates together with any phosgenation by-products.

Preferred compositions of the present invention are those wherein the isocyanate is an aromatic diisocyanate or polyisocyanate of higher functionality in particular crude mixtures of methylene bridged polyphenyl polyisocyanates containing diisocyanates, triisocyanate and higher functionality polyisocyanates. Methylene bridged polyphenyl polyisocyanates are well known in the art and have the generic formula

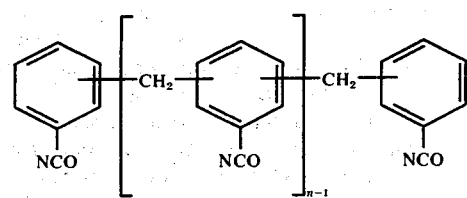

where $n$ is one or more and in the case of the crude mixtures represents an average of more than one. They are prepared by phosgenation of corresponding mixtures of polyamines obtained by condensation of aniline and formaldehyde.

Other isocyanates which can be present in the emulsions of the present invention include isocyanate ended prepolymers made by reaction of an excess of a diisocyanate or higher functionality polyisocyanate with a hydroxyl ended polyester or hydroxyl ended polyether and products obtained by reacting an excess of diisocyanate or higher functionality polyisocyanate with a monomeric polyol or mixture of monomeric polyols such as ethylene glycol, trimethylol propane or butanediol.

One preferred class of isocyanate-ended prepolymers which may form the isocyanate component of the present emulsions are the isocyanate ended prepolymers of the crude mixtures of methylene bridged polyphenyl polyisocyanates containing diisocyanates, triisocyanates and higher functionality polyisocyanates.

Non-ionic surface active agents devoid of hydroxy, amino or carboxylic acid groups useful in the present emulsions may be any such agents in particular condensates containing chains of ethylene oxide molecules and no free chain and hydroxy, amino or carboxylic acid group. These include for example condensates of alkyl phenols, long chain alcohols and amides with ethylene oxide, the end hydroxy group being for example etherified or esterified.

Of particular value are the reaction products of diisocyanates and higher functionality polyisocyanates with monoalkyl ethers of polyethylene glycols. These particular surface active agents or emulsifying agents have the formula $RO(CH_2CH_2O)_n CONHX$ wherein R is an alkyl group of from 1 to 4 carbon atoms, $n$ is an integer such that the compound contains an average of at least 5 oxyethylene groups and X is the residue of a di or polyisocyanate and contains at least one free isocyanate group. Examples of R include ethyl, propyl and butyl, preferably methyl. There must be sufficient oxyethylene groups $(CH_2CH_2O)$ present in the surface active urethane that there is an average of 5 such groups per molecule. It is preferred that $n$ represent an average of from 5 to 120.

The group X is the residue which would remain after one isocyanate group had been removed. The group X may be the residue of any diisocyanate or higher polyisocyanate and for example if the diisocyanate is a tolylene diisocyanate the residue X will be

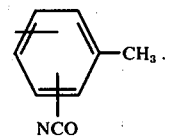

The group X preferably contains an isocyanate group.

Isocyanates from which the group X can be derived include the di and poly isocyanates listed above.

Such surface active urethanes may be manufactured by reacting an alcohol of the formula $RO(CH_2CH_2O)H$ with an isocyanate having at least two isocyanate groups, there being used at least one molar proportion of isocyanate for each molar proportion of the alcohol. Preferably an excess of the isocyanate is used.

The reaction may be carried out by adding the alcohol to the isocyanate and allowing the reaction to proceed, preferably by heating the reaction mixture at a temperature of 50°–150° C. Alternatively the reaction can be carried out at lower temperatures e.g. 25° C in the presence of a small amount of catalyst e.g. triethylene diamine.

In order to obtain emulsions according to the present invention, the above type of surface active agent may be prepared in situ in the isocyanate. Thus if it is desired to produce an emulsion of an isocyanate of the formula $X(NCO)_2$ a small amount of the polyethenoxy alcohol RO $(CH_2CH_2O)H$ may be added to a large excess of the isocyante $X(NCO)_2$ and the emulsifying agent formed in situ in the isocyanate.

In the cases where the isocyanate is a prepolymer, formation of the prepolymer and an in situ surfactant may be carried out simultaneously or as two separate steps and the prepolymer/surfactant then mixed with water to give the emulsified prepolymer.

Thus when the isocyanate present in the emulsion is to be one of the class of preferred prepolymers mentioned hereinbefore, namely a prepolymer of a mixture of methylene bridged polyphenyl polyisocyanates containing diisocyanate, triisocyanate and higher functionality polyisocyanates (referred to hereinafter as crude MDI for convenience), the emulsion of the prepolymer may be made by any of the following three methods.

1. Reaction of the MDI with the required amount of polyol to give the prepolymer followed by reaction with a small amount of the polyethenoxy alcohol $CH_3O(CH_2CH_2O)_nH$ followed by emulsification by agitation with water.

2. Reaction of the MDI with the required small amount of the polyethenoxy alcohol $CH_3O(CH_2CH_2O)_nH$ followed by reaction with the amount of polyol required to give the prepolymer followed by emulsification.

3. Reaction of the MDI with the required amounts of polyol and polyethenoxy alcohol simultaneously followed by emulsification in water.

In the above three methods the preparation of the surfactant is carried out in situ in the isocyanate, the surfactant being of the general formula $RO(CH_2CH_2O)_nX$ where X is the residue of the isocyanate and R is an alkyl group of from 1 to 4 carbon atoms.

Preferred surfactants are those derived from polyethenoxy compound $RO(CH_2CH_2O)_nH$ wherein R is methyl and $n$ is an average of from 5 to 20. Typical examples of the polyethenoxy compounds are methoxypolyethylene glycols of molecular weight 300, 400, 500 and 600.

The surfactant can of course be prepared separately and a small amount added to the prepolymer-forming mixture or to the formed prepolymer.

Formation of the prepolymers can be carried out by any of the known methods, i.e. by heating the components together or by allowing them to react an ambient temperature optionally in the presence of catalysts.

The emulsions of the prepolymers prepared by the methods described above are oil in water emulsions.

A further type of surface active agent which may be utilised is that which has the general formula:

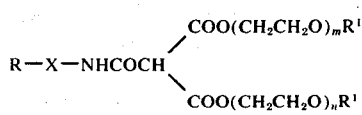

wherein X is the residue of an organic isocyanate, $R^1$ is an alkyl group of from 1 to 4 carbon atoms, $n$ and $m$ are integers such that $m + n$ is at least 10 and R which is only present when X represents the residue of a diisocyanate or a higher functionality polyisocyanate, is an isocyanate group or a group of the formula:

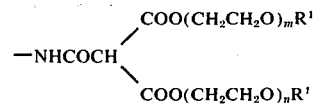

$R^1$ is preferably methyl and the sum of $m$ and $n$ is preferably between 20 and 80.

When X represents the residue of a monoisocyante the group R is absent.

X may for example be the residue of any of the isocyanates listed earlier in this specification.

These surface active agents or emulsifiers may be made by reaction of an isocyanate with a bis(alkoxy polyethenoxy) ester of malonic acid, and may if desired be prepared in situ in the isocyanate.

Preferred emulsions of the present invention are those which comprise from 99 parts to 25 parts by weight of water, from 1 part to 75 parts by weight of an organic isocyanate and a stabilising amount of a non-ionic surface active agent devoid of hydroxy, amino and carboxylic acid groups. A preferred amount of the surface active agent is from 5 parts to 15 parts by weight based on 100 parts by weight of isocyanate.

The emulsions can be prepared by conventional methods, preferably by mixing the emulsifying agent with the organic isocyanate and mixing this mixture with water. Alternatively in some cases the non-ionic surface active agent can be prepared in situ in the isocyanate and this product, diluted if desired with further isocyanate, mixed with water and the whole agitated to obtain the desired emulsion.

The emulsions of the present invention are useful as adhesives, binders and for applications in the surface coating field, such as weatherproofing wood, asbestos and concrete.

They can be used in applications where the isocyanate has previously been used as a solution in an organic solvent, either alone or in conjunction with hydroxyl group containing polyesters or polyethers.

Minor amounts of additives such as are normally employed in coating, binding and adhesive compositions may be incorporated in the emulsions of the present invention. Examples of such additions include pigments, fillers, antioxidants, resins and plasticisers and fire retardants.

The emulsions of the present invention when the isocyanate is a mixture of methylene bridged polyisocyanates (crude MDI) or a prepolymer formed from such mixture are useful for the reconstitution of scrap polyurethane foam, particularly rigid foam scrap.

Scrap rigid polyurethane foam is produced as a by product of the polyurethane rigid foam industry in the form of cut-offs, trimmings and cutting dust and is normally of little value, the pieces being of too small size for further use other than as filling. Normal physical disposal by dumping is expensive and has environmental disadvantages.

We have found that emulsions of crude MDI and prepolymers thereof according to the present invention are particularly useful for bonding together foam scrap particularly rigid foam scrap to give integrally bonded blocks of foam of any desired size or shape.

Thus as a further embodiment of the invention there is provided a process for bonding together scrap polyurethane foam which comprises coating the scrap with an aqueous emulsion of an isocyanate as hereinbefore described wherein the isocyanate is a mixture of methylene bridged polyphenyl polyisocyanates containing diisocyanates, triisocyanate and higher functionality polyisocyanate or a prepolymer of such a mixture and holding the coated scrap as a compressed mass until cured into a solid mass.

A particular use of this embodiment is in bonding together pieces of rigid foam scrap.

The term polyurethane foam used in the above description of the invention and later in the specification and claims embraces isocyanurate foams made wholly or partly by th plymerisation of isocyanates in addition to the normal polyurethane foams made by reaction of isocyanates and hydroxyl compounds.

The size of the scrap foam is not of great matter but obviously more homogeneous blocks of reconstituted foam will be obtained if the scrap material is in pieces of roughly the same size. The use of a mixture of scrap particles of graded sizes may assist in obtaining a more consolidated product which requires less compressing but may require the use of more emulsion. The pieces of scrap may conveniently range in size from 1/16" to 1".

The process is simply carried out by impregnating the pieces of scrap foam which may be in the form of small particles or even cutting dust with the oil in water emulsion and holding the mass of foam and emulsion under compression for a suitable period of time which may be easily determined by experiment. At ambient temperature several hours may be required to obtain a fully cured block of reconstituted foam by using a heated press the time required can be reduced to a few minutes. Suitable compressions are from 2 times to 5 times by volume and temperatures of 70°–100° C are suitable for a curing time of about 15 minutes.

It is preferred that the amount of water present be from 10–60% by weight of the isocyanate plus surface active agent.

The quantity of bonding agent i.e. isocyanate used may range from 10% by weight upwards on the weight of foam scrap, about 10% being the least amount found necessary to achieve a satisfactory bond using optimum distribution by spraying the emulsion on to the scrap; the upper level of usage will depend on the density required in the reconstituted material. The final density will in fact be a compromise between:
1. the amount of isocyanate used
2. degree of compression
3. density of the original foam scrap used
4. distribution of particle size in the foam scrap.

Amounts of from 10% to 70% by weight of bonding agent have been found convenient.

If increased density of reconstituted rigid foam scrap is desired, the scrap may be precompressed before bonding.

There may also be incorporated in the mixture of aqueous bonding agent and foam scrap, other particulate matter such as light weight varieties of concrete scrap, foundry sand, wood chip, cork, sawdust, expanded mica, fibrous materials and powdered fillers. Other scrap plastic materials such as scrap polystyrene may also be incorporated.

If desired silicates, silica sols and other nucleating agents and catalysts may also be incorporated.

In order to improve the fire resistance of the reconstituted foam, water-soluble fire retardants, for example, urea, ammonium salts, phosphates, borates, sodium hexametaphosphate and sodium pentaborate may be incorporated.

The compression mould may be coated with a release agent or may be lined with a preferably water permeable facing such as paper, asbestos paper or cloth or any fibrous sheet. The facing and reconstituted foam will then be bonded together to give a block of surfaced foam.

When the isocyanate to be used in a prepolymer of a mixture of methylene bridged polyphenyl polyisocyanates the prepolymer may be made by any of the routes described earlier in this specification and may be made using any of the polyetherpolyols or polyesters known to be used in the manufacture of polyurethanes. The prepolymers used are isocyanate-ended prepolymers such as well-known in the art for the manufacture of polyurethanes.

Reconstituted scrap polyurethane foam made by the above process is normally of higher density than unreconstituted foam and is suitable for flooring, for example in refrigerators and freezers in addition to being useful for thermal insulation generally.

The invention is illustrated by the following examples in which all parts and percentages are by weight except where otherwise stated.

EXAMPLE 1 a. 1100 parts of a monomethyl ether of polyethylene glycol (average mol wt. 1100) at 100° C were added dropwise to 250 parts of diphenylmethane-4,4'-diisocyanate also at 100° C, with stirring. The mixture was stirred for 30 minutes at 100° C before cooling. The product was a surface active agent.

b. 90 parts of a crude mixture of methylene bridged polyphenyl polyisocyanates were mixed with 10 parts of the surface active agent as prepared in Example 1(a). This mixture was emulsified into 100 parts of water using a high speed agitator. The emulsion was useful for coating a variety of substrates, and as a binder.

EXAMPLE 2 a. 1100 parts of a monomethyl ether of polyethylene glycol (average mol wt. 1100) at 100° C were added dropwise to 287 parts of a crude mixture of methylene bridged polyphenyl polyisocyanates (containing 29.27% isocyanate groups), also at 100°C, with stirring. The mixture was stirred for 30 minutes at 100°C before cooling. The product was a surface active agent.

b. 90 parts of a crude mixture of methylene bridged polyphenyl polyisocyanates were mixed with 10 parts of the surface active agent as prepared in Example 2(a). This mixture was emulsified into 100 parts of water using a high speed agitator. The emulsion was useful for coating a variety of substrates and as a binder.

EXAMPLE 3

90 parts of a commercially available mixture of 2,4- and 2,6- tolylene diisocyanates (80:20 ratio) were mixed with 10 parts of the surface active agent prepared in Example 1(a). This mixture was then emulsified into 200 parts of water using a high speed agitator, and the emulsion was suitable for use in coating.

EXAMPLE 4

10 parts of a monomethylether of polyethylene glycol (average mot wt. 1000) at 100° C were added, with stirring, to 90 parts of an 80:20 mixture of 2,4- and 2,6-tolylene diisocyanates also at 100° C. The mixture was heated for 30 minutes at 100° C before cooling. The product was emulsified into 200 parts of water using a high speed agitator. This is an example of in situ preparation of an emulsifying agent in a bulk of the isocyanate to be emulsified. The emulsion was useful for coating a variety of substrates.

EXAMPLE 5 a. 620 parts of a monomethylether of polyethylene glycol (average mol wt. 620) were added dropwise at 100° C to 287 parts of a crude mixture of methylene bridged polyphenyl polyisocyanates (containing 29.27% isocyanate groups) also at 100° C with stirring. The mixture was stirred for ½ hour at 100° C before cooling. The product was a surface active agent.

b. 90 parts of a crude mixture of methylene bridged polyphenyl polyiscoyanates were mixed with 10 parts of the surface active agent as prepared in Example 5(a). The mixture was emulsified into 200 parts of water using a high speed agitator. The emulsion was useful for coating a variety of substrates.

EXAMPLE 6

5 parts of a monomethylether of polyethylene glycol (average mol wt. 620) were added dropwise to 95 parts of a crude mixture of methylene bridged polyphenyl polyisocyanate with stirring at 100° C and then cooled. The product could be emulsified into water. Emulsions were prepared in water containing up to 75% of the polyisocyanate. This is an example of in situ preparation of a surfactant in a bulk of a high functionality polyisocyanate. The emulsions were useful for coating a variety of substrates.

EXAMPLE 7

As example 6 but 0.5% of triethylene diamine (based on the glycol) added to the glycol and the ensuing reaction with the polyisocyanate carried out at room temperature. This is a further example of in situ preparation of a surfactant in a bulk of a high functionality polyisocyanate. Emulsions in water were prepared using this product containing up to 50% of the polyisocyanate. The emulsions were useful for coating a variety of substrates.

EXAMPLE 8 a. 2000 parts of a monomethylether of polyethylene glycol (average mol wt 1000) were mixed with 160 parts of diethyl malonate and 2 parts of tetrabutyl titanate. The mixture was then heated, with stirring, and in a nitrogen stream, at 165° C for 4 hours. The product was filtered whilst hot. The product was a surface active agent.

b. 10 parts of the bis(methoxy polyethenoxy) malonate as prepared in Example 8(a) were stirred with 90 parts of a crude mixture of methylene bridged polyphenyl polyisocyanates at 100° C for 1 hour. The product was emulsified into 50 parts of water. This is an example of in situ prepartion of a surface active agent in a bulk of the high functionality polyisocyanate to be emulsified. The emulsion was useful for coating a variety of substrates.

EXAMPLE 9

An isocyanate ended prepolymer containig 26% isocyanate groups was prepared by reacting a crude mixture of methylene bridged polyphenyl polyisocyanates with a hydroxyl ended polyester. 90 parts of this prepolymer were mixed with 10 parts of a methyl ether of polyethylene glycol (average mol wt 620) and 0.5 parts of triethylene diamine. The mixture was stirred for 5 minutes at room temperature and could then be emulsified into water. The emulsion was useful for coating a variety of substrates.

EXAMPLE 10

An isocyanate ended prepolymer was prepared by adding 500 parts of an oxyalkylated glycerol (average mol wt 1000) dropwise to 1025 parts of a crude mixture of methylene bridged polyphenylpolyisocyanates (containing 29.27% of isocyanate groups) which was stirred at 100° C. The prepolymer was then mixed with a further 922.5 parts of the crude polyisocyanate reacted with 102.5 parts of a methyl ether of polyethylene glycol (average mol wt 620). The product could be emulsified into water. The emulsion was useful for coating a variety of substrates.

EXAMPLES 11, 12 AND 13

A mixture of methylene bridged polyphenyl polyisocyanates containing diisocyanate, triisocyanate and higher polyisocyanates made by phosgenation of an aniline/formaldehyde condensation product obtained by condensation in the presence of hydrochloric acid was reacted at 100° C for 30 minutes with a monomethylether of polyethylene glycol (average molecular weight 300). This mixture of polyisocyanates was emulsified with water in the proportions shown in Table I to give emulsions which were mixed with foam scrap in the amount shown. The mixture was then compressed to the degree shown in the table and held under compression for the times given in the table. In one case a Catalyst Armeen DM116D was incorporated.

The reconstituted foam blocks were removed from the moulds and their physical properties were recorded in the table.

TABLE I

| | Example 11 | Example 12 | Example 13 |
|---|---|---|---|
| Rigid polyurethane foam scrap | 100 | 100 | 100 |
| Polyisocyanate + methoxy polyethylene glycol | 60 | 30 | 27 |
| Water | 20 | 20 | 13 |
| Armeen DM116D | — | — | 0.07 |
| Compression | 5x | 3x | 2x |
| Compression time | & 1½ hours at 20° C | & 1 hour at 20° C | & 15 minutes at 80° C |
| Density mg/m$^3$ | & 90 | & 75 | & 60 |
| Compression strength | | | |
| 10% | 88 | 55 | 87 |
| 25% | 154 | 152 | 129 |

TABLE 1-continued

| | Example 11 | Example 12 | Example 13 |
|---|---|---|---|
| Modulus kN/m² | 984 | 573 | 1025 |

EXAMPLE 14

100 parts of a mixture of methylene bridged polyphenyl polyisocyanates as in Example 1 was mixed with
  5 parts methoxy polyethylene glycol (MW 300)
  30 parts oxypropylated glycerol (MW 1000)
  20 parts Tris(chloropropyl) phosphate (fire retardant)
  0.3 parts Armeen DM16D (tertiary amine catalyst)

The above mixture was allowed to react for 6 hours at room temperature to form prepolymer and surfactant simultaneously.

100 parts of the above product was emulsified with 50 parts water and 400 parts of scrap polyurethane foam coated with the emulsion whilst under agitation. The whole was then placed in a mould coated with paper and compressed to 3 times compression at 70° C.

After 15 minutes the reconstituted foam was removed from the mould and had set to a foam slab bonded to the paper.

EXAMPLE 15

100 parts of a mixture of methylene bridged polyphenyl polyisocyanates containing diisocyanate, triisocyanate and higher functionality polyisocyanates made by condensing aniline and formaldehyde in the proportions 2/1 in the presence of hydrochloric acid, were mixed with 5 parts of methoxypolyethylene glycol and 30 parts of oxypropylated glycerol of Molecular Weight 1000. The mixture was heated to 60° C and held at this temperature for 24 hours with intermittent agitation to give simultaneous formation of prepolymer and surfactant.

100 parts of the above product was emulsified with 200 parts water.

Asbestos cement sheet was coated with the above emulsion by brush application and the coating allowed to air-dry. After about 4 hours the resultant surface coating had a glossy hard bubble free surface and had excellent adhesion to the substrate.

Incorporation of pigments via the aqueous phase gave coloured coatings of equal quality.

What we claim is:

1. An oil-in-water emulsion comprising,
  a. from 99 to 25 parts by weight of water;
  b. from 1 to 75 parts by weight of an aromatic polyisocyanate; and
  c. a stabilizing amount of a non-ionic surface active agent having the formula $$RO(CH_2CH_2O)_nCONHX$$

wherein R is alkyl containing from 1 to 4 carbon atoms, $n$ is an integer such that the surface active agent contains an average of from 5 to 120 oxyethylene groups and X is the residue of a di- or polyisocyanate and contains at least one free isocyanate group.

2. An oil-in-water emulsion as claimed in claim 1 wherein the aromatic isocyanate is a crude mixture of methylene bridged polyphenyl polyisocyanates.

3. An oil-in-water emulsion as claimed in claim 1 wherein the surface active agent contains an average of from 5 to 20 oxyethylene groups.

4. An oil-in-water emulsion as claimed in claim 3 wherein R is methyl.

5. An oil-in-water emulsion as claimed in claim 1 wherein there is present from 5 to 15 parts by weight of surface active agent based on the weight of isocyanate.

6. Process for the manufacture of the oil-in-water emulsion of claim 1 wherein the non-ionic surface active agent is initially mixed with the organic isocyanate and this mixture is then mixed with the water.

7. A process for the manufacture of the oil-in-water emulsion of claim 1 comprising reacting a polyethenoxy alcohol having the formula $$RO(CH_2CH_2O)_nH$$

wherein R is alkyl containing from 1 to 4 carbon atoms and $n$ is an integer such that the polyethenoxy alcohol contains an average of from 5 to 20 oxyethylene groups, with the isocyanate (b) in sufficient quantity to form the surface active agent (c) in situ in said isocyanate, and agitating the resulting mixture with water.

* * * * *